United States Patent [19]
Horton et al.

[11] Patent Number: 6,060,322
[45] Date of Patent: May 9, 2000

[54] METHOD FOR IDENTIFICATION OF RETICULATED CELLS

[75] Inventors: Allan Horton, Miami; James L. Wyatt, Plantation, both of Fla.

[73] Assignee: Coulter International Corp., Miami, Fla.

[21] Appl. No.: 09/175,493

[22] Filed: Oct. 20, 1998

[51] Int. Cl.$^7$ .................................................. G01N 33/48
[52] U.S. Cl. ............................... 436/63; 436/8; 436/10; 436/17; 436/164; 436/166; 436/172; 435/2
[58] Field of Search .................................. 436/8, 10, 17, 436/18, 63, 164, 166, 172, 800; 252/408.1; 435/2, 4, 6, 29, 34, 39

[56] References Cited

U.S. PATENT DOCUMENTS

| | | | |
|---|---|---|---|
| 3,962,125 | 6/1976 | Armstrong | 436/10 X |
| 4,883,867 | 11/1989 | Lee et al. | 436/10 X |
| 4,957,870 | 9/1990 | Lee et al. | 436/63 |
| 4,985,174 | 1/1991 | Kuroda et al. | 252/408.1 |
| 5,075,556 | 12/1991 | Fan et al. | 250/459 |
| 5,284,771 | 2/1994 | Fan et al. | 436/10 |
| 5,350,695 | 9/1994 | Glella et al. | 436/63 |
| 5,360,739 | 11/1994 | Fan et al. | 436/63 |
| 5,411,891 | 5/1995 | Fan et al. | 436/63 |
| 5,438,003 | 8/1995 | Colella et al. | 436/63 |
| 5,633,167 | 5/1997 | Fan et al. | 436/17 |
| 5,639,666 | 6/1997 | Shenkin | 436/63 |
| 5,686,309 | 11/1997 | Frank et al. | 436/66 |
| 5,691,204 | 11/1997 | Kim et al. | 436/63 |
| 5,733,784 | 3/1998 | Studholme et al. | 436/63 |
| 5,773,299 | 6/1998 | Kim et al. | 436/63 |

OTHER PUBLICATIONS

Robinson et al. *British Journal of Haematology,* vol. 100, pp. 351–357, Feb. 1998.
Houwen et al. *Labatory Hematology,* vol. 1:53, 1995.
Houwen et al. *Blood,* vol. 88:319a, 1996.
Carter et al. (1989) "Counting reticulocytes by flow cytometry: use of thiazole orange," *Clin. Lab. Haemat.,* 11:267–271.
Lee et al., (1986) "Thiazole orange: a new dye for reticuloyte analysis," *Cytometry,* 7:508.
Richards et al. (1996) "Measurement of reticulated platelets following periphal blood progenitor cell and bone marrow transplantation: implications for marrow reconstitution and the use of thrombopoietin," Bone Marrow Transplantation, 17:1029–1033.
Seligman et al. (1983) "Automated anaylsis of reticulocytes using fluorescent staining with both acridine orange and an immunofluorescence technique," *American Journal of Hematology,* 14:57–66.
Thaer et al. (1970) "Microfluorometric analysis of the reticulocyte population in peripheral blood of mammals," *Cytology Automation,* DMD Evans (Ed.), E&S Livingstone, Edinburgh, pp. 180–195.
Vander et al. (1963) "Reticulocyte counts by means of fluorescence microscopy," *J. Lab. & Clin. Med.,* 62:132–140.
Van Hove et al. (1990) "Reticulocxyte count using thiazole orange. A flow cytometry method," *Clin. Lab. Haemat.,* 12:287–299.
Watanabe et al. (1995) "Automated measurement of reticulated platelets in estimating thrombopoiesis," *Eur. J. Haematol.,* 54:163–171.

*Primary Examiner*—Maureen M. Wallenhorst
*Attorney, Agent, or Firm*—Mitchell E. Alter

[57] ABSTRACT

A reagent composition and method is provided for identification of reticulated cells from other cell types in a blood cell sample by using optical measurement. More particularly, the reagent composition contains a nucleic acid dye and sphering agent. More particularly, the method enables the identification of reticulated platelets and reticulated erythrocytes. In addition, the method provides for a concurrent determination of cell by cell hemoglobin of the reticulated erythrocytes and mature erythrocytes in the blood cell sample.

10 Claims, 5 Drawing Sheets

Automated Reticulocyte Assay with Reagent Composition
Compared to Assay without Reagent Composition

METHOD FOR IDENTIFICATION OF RETICULATED CELLS

BACKGROUND OF THE INVENTION

1. Technical Field of the Invention

The present invention relates to a reagent composition and method for identification of reticulated cells from other cell types in a blood cell sample by using optical measurement. More particularly, the reagent composition comprises a nucleic acid dye and sphering agent. More particularly, the method enables the identification of reticulated platelets and reticulated erythrocytes. In addition, the method provides for a concurrent determination of cell by cell hemoglobin in the blood cell sample by suitable electrical and optical measurements.

2. Discussion of the Prior Art

Reticulated cells are defined as being any blood cell which contains reticulum. Reticulated cells include reticulated erythrocytes and reticulated platelets. Reticulated erythrocytes are commonly known as reticulocytes.

The identification of reticulated cells has focused on reticulocyte analysis. Prior art in reticulocyte enumeration methods suitable for automated hematology is based on reagents containing acridine orange (AO), oxazine 750, thiazole orange (TO) and its derivatives and coriphosphine-O (CPO). Acridine orange, thiazole orange and coriphosphine-O are all brightly fluorescent when bound to RNA. Each of these dyes are cell membrane permeant, i.e. they transport through the membrane of the reticulocyte cells freely. This makes them attractive and useful for automated hematology application. However, each of these reagents present their own methods of analysis and problems.

Specific examples using acridine orange (AO) are cited in U.S. Pat. Nos. 5,075,556; 5,360,739 and 5,411,891 each to Fan et al.; and cited in publications to Vander et. al., (1993) J. Lab. Clin. Med, 62:132, Thaer et. el. (1970) "Microfluorometric analysis of the reticulocyte population in peripheral blood of mammals" in Cytology Automation, DMD Evans (ed.), E&S Livingistone, Edinburgh (1970), pp. 180–195; and Seligman et. al., (1983) American J. Hematol., 14:57–66].

Specific examples using oxazine 750 are shown in U.S. Pat. Nos. 5,284,771 and 5,633,167 each to Fan et al.; and oxazine 750 or new methylene blue shown in U.S. Pat. Nos. 5,350,695 and 5,438,003 each to Colella et al.

Specific examples using thiazole orange (TO) are shown in U.S. Pat. Nos. 4,883,867 and 4,957,870; and cited in publications Cytometry (1986) 7:508 L. G. Lee et. al.; Van Hove et. al. (1990) Clin. Lab. Hemat., 12:287–299; Carter et. al. (1989) Clin. Lab. Haemat, 11:267–271].

Specific examples using coriphosphine-O (CPO) are shown in U.S. Pat. No. 5,639,666 to Shenkin.

In addition, other reagents and automated methods have been developed for analysis of reticulocytes. U.S. Pat. No. 4,985,174 to Kuroda et al. disclose a reagent containing auramine-O for the fluorescent staining of reticulocytes in a sample of whole blood to permit determination of reticulocytes by means of a flow cytometer. U.S. Pat. Nos. 5,773, 299 and 5,691,204 each to Kim et al. disclose an unsymmetrical cyanine dye.

Another form of reticulated cells are reticulated platelets. Reticulated platelets are released into the peripheral blood following megakaryocytic fragmentation. Newly formed platelets, although anucleated, contain some rough endoplasmic reticulum and messenger RNA (mRNA) and are also able to synthesize small amounts of protein. Their measurement has considerable clinical utility for monitoring thrombopoiesis and platelet turnover as the mRNA is unstable and degrades within twenty four hours in animal models.

Prior art in reticulated platelet analysis has been based on thiazole orange as shown in Robinson et al. (1998) "Flow cytometric analysis of reticulated platelets: evidence for a large proportion of non-specific labeling of dense granules by fluorescent dyes" in British Journal of Haematology, 100, pp. 351–357 and Richards, et al. (1996) "Measurement of reticulated platelets following peripheral blood progenitor cell and bone marrow transplantation: implications for marrow reconstitution and the use of thrombopoietin" Bone Marrow Transplantation, 17 pp. 1029–1033. In addition auramine-O has been used in Watanabe et al. (1995) "Automated measurement of reticulated platelets in estimating thrombopoiesis" Eur. J. Haematol 54 pp. 163–171. Both dyes are a fluorescent nucleic acid dye excitable at 488 nm and are suitable for argon lasers in standard flow cytometers.

Prior to the invention disclosed herein, prior art determinations of reticulated platelets did not conform to any standardized results or methodologies. Fundamentally, each laboratory set its own standard of practice and measurement system. Prior analysis led to the conclusion among some laboratories, but not all, that reticulated platelets constituted approximately 2% to 20% of a normal platelet population.

Thus, there exist a need for a reagent composition with specificity and method that enables an accurate determination of reticulated cells in less than 60 seconds. In addition, the reagent and method finds particular utility for the automated method for the identification of reticulated platelets.

SUMMARY OF THE INVENTION

In view of the foregoing discussion, an object of the invention is to provide a reagent composition and method for identification of reticulated cells from other cell types in a blood cell sample by using an optical measurement.

In accordance with one aspect of the present invention, a reagent composition is provided for identifying subclasses of reticulated cells comprising coriphosphine-O; a sphering agent, and a buffer.

According to another aspect of the present invention a method for identifying reticulated cells in a blood cell sample containing reticulated cells and non reticulated blood cells on an automated hematology analyzer is provided. The method comprises mixing a blood cell sample containing reticulated cells with a reagent composition comprising a metachromatic dye and a sphering agent to form a suspension of cells; incubating the suspension of cells for less than 60 seconds to allow the reagent composition to stain single stranded and double stranded nucleic acid contained in the blood cells; exciting said sample with light excitation wavelength; measuring the presence of a first fluorescence signal in the suspension of cells, against the presence of second fluorescence signal gated on at least one parameter selected from light scatter, direct current, radio frequency and fluorescence, said at least one parameter being used to identify leukocytes, erythrocytes, thrombocytes; and identifying the number of reticulated cells in the sample from said measurement.

As will be better appreciated from the following Detailed Description of Preferred Embodiments, the invention is advantageous compared to the prior art in that it provides a novel method of identification of reticulated cells in less than 60 seconds and is particularly advantageous for identifying reticulated platelets.

The invention and its various advantages will be better understood from the ensuing detailed description of preferred embodiments, reference being made to the accompanying drawings in which like reference characters denote like parts.

DETAILED DESCRIPTION OF PREFERRED EMBODIMENTS

The present invention relates to a reagent composition and method for differentiation of reticulated cells and also for a method for concurrent differentiation of cell by cell hemoglobin concentration in a blood cell sample. More particularly, the method provides for the identification of reticulated platelets.

In a first embodiment, the reagent composition of the present invention comprises coriphosphine-O; a sphering agent, and a buffer.

It has been found that coriphosphine-O is an effective dye for staining reticulated cells. Coriphosphine-O is a fluorochrome dye that does not precipitate intracellular ribonucleic acid of a reticulocyte or a reticulated platelet. Coriphosphine-O (CPO) is also known as basic yellow seven and is available from Pfaltz & Bauer, Inc. Division of Aceto Corporation, Waterbury, Conn.

The dye functions to delineate reticulated cells using fluorescence and light scatter in a flow cytometer. Additionally, the invention permits the rapid staining of these classes of cells for analysis in instrumentation equipped with fluorescence and another measurement modality selected from light scatter, direct current (DC volume) and radio frequency (RF).

By using a reagent composition containing coriphosphine-O as the dye and a sphering agent, it is possible to rapidly detect and enumerate reticulated cells in a whole blood sample. The reagent composition offers the additional advantage of differentially staining reticulocytes and reducing interference of analysis by sample interferences, such as cellular granules, nucleated red blood cells, and Howell-Jolly Bodies. In addition, the reagent composition makes possible detection and enumeration of reticulated platelets in a whole blood sample.

The concentration of the coriphosphine-O dye in the reagent composition ranges from approximately 0.05 µg/ml. to approximately 50 µg/ml. Preferably the dye in the reagent composition ranges from 0.5 µg/ml to 30 µg/ml, and most preferably 1 µg/ml to 15 µg/ml. If the concentration of the dye exceed 50 µg/ml, the background fluorescence interferes with the measurement of the reticulated cell. If the concentration of the dye is less than 0.05 µg/ml, the cells are insufficiently stained for accurate detection.

In addition, the reagent composition contains a sphering agent. The sphering agent is used in an amount effective to cause the reticulated cells, such as reticulated platelets and reticulated erythrocytes, and red blood cells to isovolumetrically sphere to eliminate orientation artifacts in analysis of the reticulated cells. Desirably, the sphering reagent is a zwitterionic surfactant which isovolumetrically spheres the red blood cells and reticulated cells. The zwitterionic sphering agent is preferably an alkyl amido betaine or an alkyl betaine such as lauroamidopropylbetaine, cocoamidopropylbetaine and cocoamidosulfobetaine. Other sphering agents are N-tetradecyl-N-, N-dimethyl-3-ammonio-1-propanesulfonate and N-dodecyl-N, N-dimethyl-3-ammonio-1-propanesulfonate, n-dodeceyl-D-maltoside, polyoxypropylene-polyoxethylene block copolymer ("Pluronic F® 127"), n-tetradecyl-D-maltoside, decanoyl-N-methyl-glucamide, n-dodecyl-D-glucopyranoside and n-decyl-D-glucopyranoside. Currently, a preferred sphering agent is dodecyl-β-D-maltoside, which suitably is in solution with a buffer such as phosphate buffered saline.

To effectively isovolumetrically sphere the reticulated cells and red blood cells within a blood sample, the concentration of the sphering agent in the composition ranges from approximately about 3 µg/ml to about 40 µg/ml, preferably from about 10 µg/ml to about 30 µg/ml and most preferably from about 15 µg/ml to about 25 µg/ml. The osmolality of the reagent composition ranges from 250 to 350 mOsm to effective enable isovolumetric sphering. The osmolality can be adjusted by techniques known to those skilled in the art using salts and other osmotically active agents. Suitable osmolality agents include mono-,or di-, valent alkali salts which do not precipitate or react adversely with the dye in the reagent composition.

The reagent composition further contains other components, such as buffers, preservatives and the like. Suitable buffers include those, which maintain the pH of the composition in the range of about 6 to about 9, preferably 6.5 to 7.7. Examples of suitable buffers include phosphate buffered saline or isotonic saline, such as ISOTON®II, U.S. Pat. No. 3,962,125, Coulter Corporation, Miami, Fla., or the like. The buffer is selected such that it does not contain a protein or a fixative. It has been found that a protein buffer will interfere with a cell by cell hemoglobin determination. In addition, a buffer containing a fixative will interfere with a determination of reticulated cells.

In a second embodiment of the present invention, a method is provided for identification of reticulated cells in a blood cell sample containing reticulated cells and non reticulated blood cells on an automated hematology analyzer. The method comprises mixing a blood cell sample containing reticulated cells with a reagent composition comprising a metachromatic dye and a sphering agent to form a suspension of cells; incubating the suspension of cells for less than 60 seconds to allow the reagent composition to stain single stranded and double stranded nucleic acid contained in the blood cells; exciting said sample with light excitation wavelength; measuring the presence of a first fluorescence signal in the suspension of cells, against the presence of second fluorescence signal gated on at least one parameter selected from light scatter, direct current, radio frequency and fluorescence, said at least one parameter being used to identify leukocytes, erythrocytes, thrombocytes; and identifying the number of reticulated cells in the sample from said measurement.

In the method of this invention, a blood sample, which may be whole blood or a blood fraction, containing reticulated cells and non reticulated cells, is stained with the reagent composition containing coriphosphine-O by mixing the blood sample with the reagent composition. The volumes of blood sample and reagent composition used are such that the concentrations of cells are sufficient to run through the instrument. Thus, the blood is diluted with the reagent composition in the range of 1:100–1:10,000, preferably 1:500–1:5,000, most preferably 1:1,000–1:2,000. The sample is then incubated at room temperature with the reagent composition for less than 60 seconds to allow the reagent composition to stain single stranded and double stranded nucleic acid in the blood cells. Preferably, the incubation is for less than 30 seconds, and more preferably less than 15 seconds. Most preferred, the incubation is from 5 to 10 seconds. The diluted and stained blood sample is then run through a flow cytometer or other similar hematology analyzer. It has been found that coriphosphine-O is a vital stain, and, accordingly, fixation is not required.

Coriphosphine-O is a metachromatic dye. When coriphosphine-O is unbound from ribonucleic acid (RNA), it provides little or no red fluorescence when excited, and exhibits a strong absorption peak at about 490 nm. When coriphosphine-O is bound to RNA in the reticulated cells, the optical properties thereof change dramatically. In particular, coriphosphine-O when bound to RNA in the reticulated cells exhibits a strong red fluorescence when excited. The excitation maximum is at about 490 nm and the emission maximum is at about 630 to about 700 nm, giving a Stokes shift of about 160 nm. Since the bound coriphosphine-O is excited at about 490 nm, the light source can be an argon ion laser or a frequency doubled diode laser having a green emission at approximately 532 nm. Preferably a green emission laser is employed in the method of this invention because the ratio of excitation to emission is enhanced upon RNA binding compared to the use of an argon ion laser at approximately 488 nm. Although excitation may be effected at other wavelengths, reticulated cells stained with coriphosphine-O are preferably excited at a wavelength of from about 450 nm to about 540 nm, and preferably 525 to 535 nm. It has been further found that at excitation above 540 nm, there is insufficient excitation of the RNA bound coriphosphine-O to enable detection.

Coriphosphine-O when unbound to deoxyribonucleic acid (DNA) in the non reticulated cells, such as white blood cells, provides little or no green fluorescence when excited. However, when coriphosphine-O is bound to DNA in white blood cells and excited, the cells exhibit a strong green fluorescence. The lack of fluorescence of the coriphosphine-O dye when not bound to nucleic acid provides low background fluorescence and allows an operator to select a fluorescence threshold (or "gate") for an automated flow cytometer.

Moreover, when coriphosphine-O is bound, the amount or intensity of green fluorescence is proportional to the amount of background or nonspecific staining due to the binding of coriphosphine-O to other cellular structures. These other cellular structures or elements include abnormal DNA and subcellular vesicle such as lysosomes, endosomes, and granules. Each of these elements binds the coriphosphine-O differently, resulting in different amounts of fluorescence. However, only single-stranded RNA will bind coriphosphine-O and fluoresce red as a result of the specified incubation period.

It has been determined that reticulated platelets and mature platelets contain adenosine diphosphate (ADP) granules which stain with nucleic acid dyes. When stained, the granules will fluoresce in the red spectrum. It has been discovered that the kinetics of staining favor the RNA staining over the non specific staining of the ADP containing granules. It has been found that the rapid staining of less than 60 seconds preferentially stains the RNA of reticulated platelets over ADP granules contained in all platelets.

In performing the method of this invention, we determine the maximum amount of green fluorescence of mature red blood cell population as a threshold for both red blood cells and reticulated cells. For reticulated platelets, a threshold greater than a threshold used for mature red cells is used because reticulated platelets contain numerous cellular structures which contribute to a higher level of background fluorescence than observed in erythrocytes. All other cells will fluoresce green above the threshold used for DNA. The difference in intensity of green fluorescence offers the advantage of differentially staining cells enabling one to gate-out non-specific cells, such as white blood cells.

The reagent composition provides a nearly linear relationship between the fluorescent signal measured for an individual reticulated cell and its nucleic acid content. Clinically, this provides the physician with additional information beyond the reticulated cell count in that RNA content is a function of reticulated cell age. Accordingly, by using the reagent composition of this invention, a clinician has the ability to obtain reticulated cell age, as well as a reticulated erythrocyte and reticulated platelet count.

Reticulated cells stained with the reagent composition of this invention are preferably enumerated in an automated flow cytometer, but can also be counted by a manual procedure or automated microscopy.

The fundamental concept of flow cytometry is essentially the passing of cells, one at a time, through a specific sensing region. By means of hydrodynamic focusing, single cells are passed through the sensing zone, which consists of a focused laser light source and a detection system for the measurement of scattered and fluorescent light and electronic properties. Automatic flow cytometers are well known in the art, and the present invention is not limited to the use of any particular flow cytometer.

Figure 4:
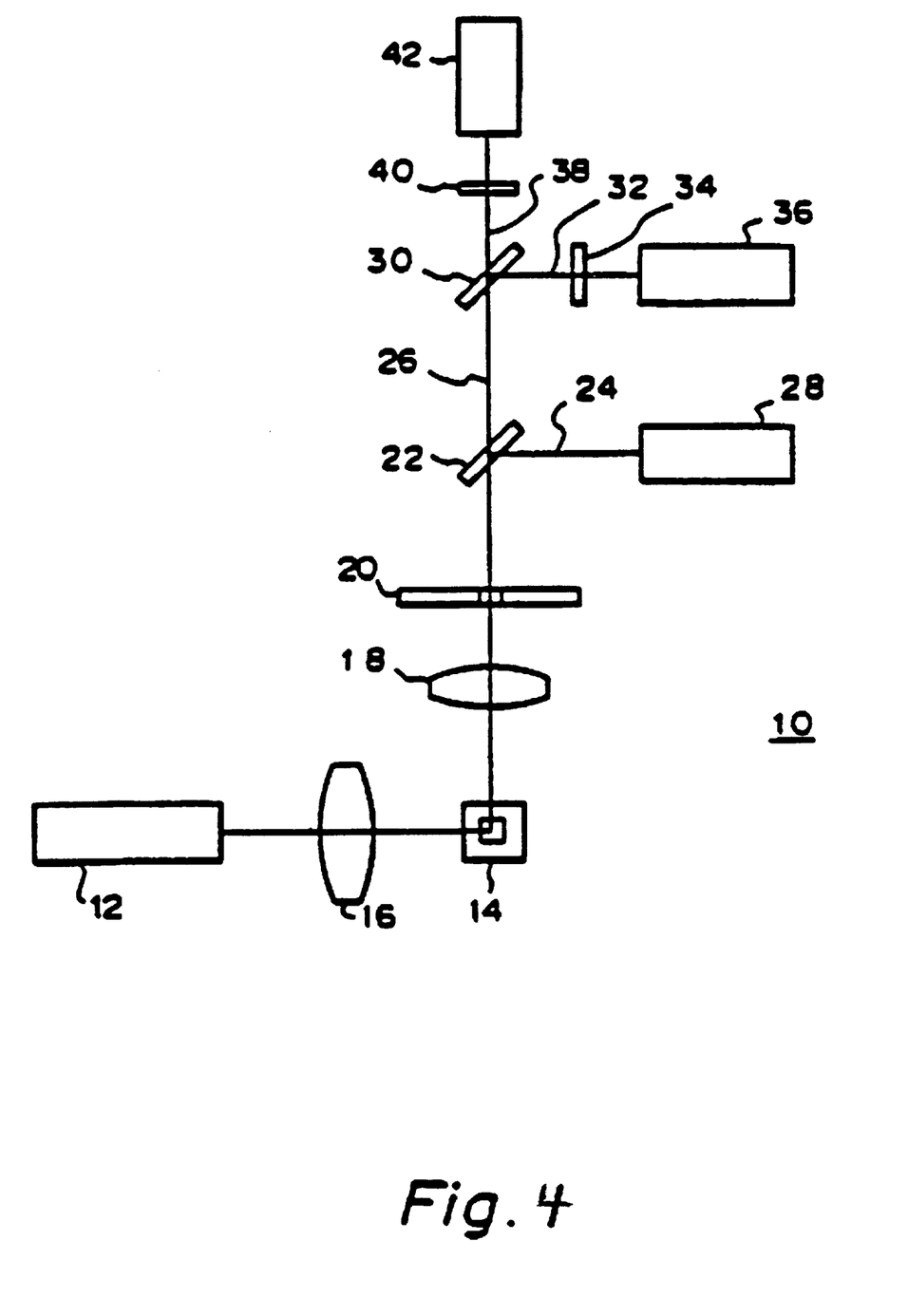
FIG. 4 depicts a schematic diagram of the optics of a flow cytometer that can be employed in implementing the method of the present invention.

A specific example of the optics of a flow cytometer employed in the present invention is described with reference to FIG. 4. The optics shown in FIG. 4 are used in a flow cytometer designed for measuring forward light scatter, right-angle scattered light, red fluorescence (FL2)) and green fluorescence (FL1). The optic generally indicated by 10 uses a laser 12 as a light source and it operates at a wavelength of approximately 530 nm. Light emitted from the laser 12 is converged by a cylindrical lens 16 and illuminates a blood sample flowing through a flow cell 14 in a conventional means.

When the stained blood cells in the sample are irradiated by the laser light, they produce scattered light and fluorescence. The right-angle scattered light and the fluorescence (FL1 and FL2) are converged with a condenser lens 18 and pass through an aperture 20 to fall upon a dichroic mirror 22. The dichroic mirror 22 reflects the right-angle scattered light 24 and transmits the fluorescence 26. The right-angle scattered light 24 reflected from the dichroic mirror 22 is detected in a photomultiplier tube or photodiode 28. The forward light scatter is detected by means of a suitable sensor detected in a photomultiplier tube or photodiode not shown. Of the fluorescence 26 that passes through the dichroic mirror 22, green fluorescence 32 is reflected by a dichroic mirror 30 and red fluorescence 38 is transmitted through that mirror. The reflected green fluorescence 32 passes through a coated optical filter 34 and is detected in a photomultiplier tube 36. The transmitted red fluorescence 38 passes through a coated optical filter 40 and is detected in a photomultiplier tube 42.

Thus, for example, reticulated cells stained with the reagent composition of this invention can be detected and enumerated in a COULTER®XL™ flow cytometer sold by Coulter Corporation, Miami, Fla. In using the automated flow cytometer, fluorescence distribution of mature blood cells is used to determine a fluorescent threshold for enumeration of reticulated cells.

The use of an automated flow cytometer for detection and enumeration of reticulated erythrocytes stained with the reagent composition of this invention provides results which closely correlate with results obtained by a known standard method for enumerating reticulocytes which uses new methylene blue or acridine orange, or thiazole orange.

However, previous measurements of reticulated platelets are believed to be in error by as much as 50%. Prior measurement with nucleic dye assumed that all stained platelets were reticulated. However, according to this invention, it has been discovered that the stained platelets result from a combination of specific and non specific bound nucleic acid bound dye. Therefore, the reagent composition and method of this invention provide the opportunity to distinguish between specifically stained reticulated platelets and non specifically stained platelets.

In addition, the method of this invention provides for a concurrent determination of cell by cell hemoglobin in the blood cell sample by suitable optical and electrical measurements. The identification of reticulated cells is performed in a focused flow cell with a sheath fluid using light scatter and fluorescence measurements. The light scatter measurements can be combined with cellular volume information to determine the hemoglobin concentration within an erythrocyte on an individual cell basis to provide a cell by cell hemoglobin determination.

By employing the method of this invention for the analysis of a blood cell sample, one is able to obtain the cell by cell hemoglobin since the reagent composition does not interfere with data collection. Appropriate gating of the reticulated erythrocytes, then enables a determination of cell by cell hemoglobin of the reticulated erythrocytes using those same light scatter and volume measurements used in initial gating of cell populations.

The method of this invention can be further understood by reference to the following examples. However, it will be appreciated that the invention is not limited to the described examples.

EXAMPLE I IDENTIFICATION OF RETICULATED CELLS

A patient blood sample was collected into triphosphate EDTA (K3EDTA). 0.002 mL of patient blood sample was added to 2.0 mL of the reagent composition. The sample was mixed and allowed to incubate at room temperature at approximately 25 seconds. The blood sample was then analyzed on a flow cytometer excited at 488 nm.

Forward light scatter (FS), side scatter (SS) and two fluorescence (FL) parameters were measured to analyze the reticulated cells. The reticulated and non-reticulated cells are distinguished by the analysis by plotting red fluorescence against the presence of green fluorescence after gating on cell size and granularity to identify classes of cells (e.g., leukocytes, thrombocytes, and red blood cells).

Figure 1A:
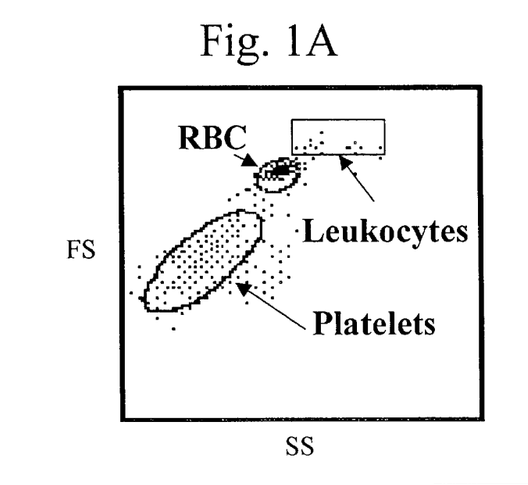
FIGS. 1A–1C are three histograms for the purpose of identification of reticulated erythrocytes according to Example 1.
Figure 1B:
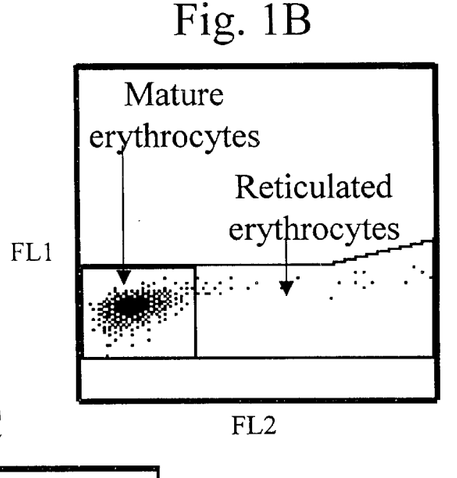
Figure 1C:
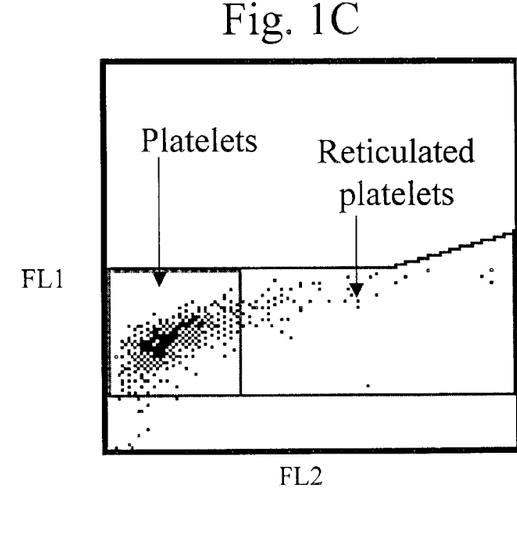

FIGS. 1A–1C show three scattergrams which depicts the analysis to determine the reticulated cell populations. FIG. 1A is an example of the light scatter histogram showing gates on red blood cell (RBC), leukocyte and thrombocyte populations. Thrombocytes are shown as Platelets in FIG. 1A. FIG. 1B displays a dot plot of the red fluorescence (FL2) versus the green fluorescence (FL1), gated on the red blood cells determined from FIG. 1A. The red fluorescence parameter shows a distinction between reticulated red cells and non reticulated red cells. The green parameter shows elimination of non red cells. FIG. 1C shows the fluorescence distribution of platelets showing a difference between mature platelets and reticulated platelets gated on the platelets determined from FIG. 1A.

EXAMPLE II IDENTIFICATION OF RETICULATED ERYTHROCYTES WITH CELL BY CELL HEMOGLOBIN

A second patient blood sample was collected into triphosphate EDTA (K3EDTA). 0.002 mL of patient blood sample was added to 2.0 mL of the reagent composition. The sample was mixed and allowed to incubate at room temperature at approximately 25 seconds. The blood sample was then analyzed on a flow cytometer excited at 532 nm.

Figure 2A:
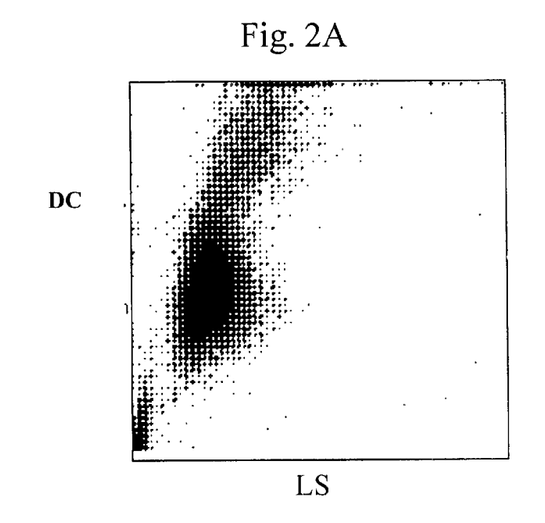
FIGS. 2A–2C are three histograms for the purpose of identification of reticulated erythrocytes with cell by cell hemoglobin according to Example II.
Figure 2B:
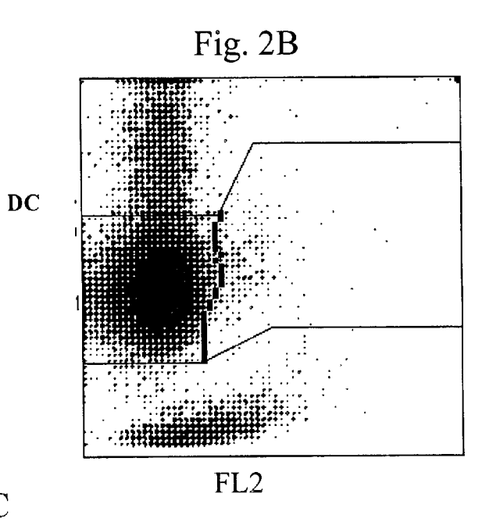
Figure 2C:
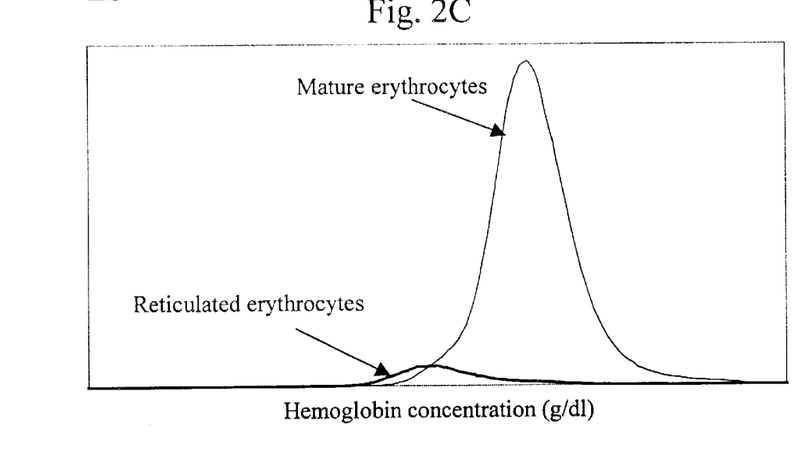

Forward light scatter (LS), direct current (DC) and fluorescence parameters were measured in an analysis of reticulated cells and non reticulated cells. Reticulated cells and non reticulated cells are distinguished by plotting DC versus FL2 as shown in FIG. 2B. The reticulated and non-reticulated cells are further distinguished in the analysis by plotting light scatter (LS) against DC shown in FIG. 2A. Using LS and DC information obtain in FIG. 2A and gating on reticulated cells and non reticulated cells from FIG. 2B, enables a determination of cell by cell hemoglobin of mature erythrocytes and reticulated erythrocytes as shown in FIG. 2C.

EXAMPLE III CHARACTERIZATION OF RETICULATED CELL ASSAY

A third patient blood sample was collected into triphosphate EDTA (K3EDTA). 0.002 mL of patient blood sample was added to 2.0 mL of the reagent composition. The sample was mixed and allowed to incubate at room temperature at approximately 25 seconds. The blood sample was then analyzed on a flow cytometer excited at 532 nm.

Figure 3A:
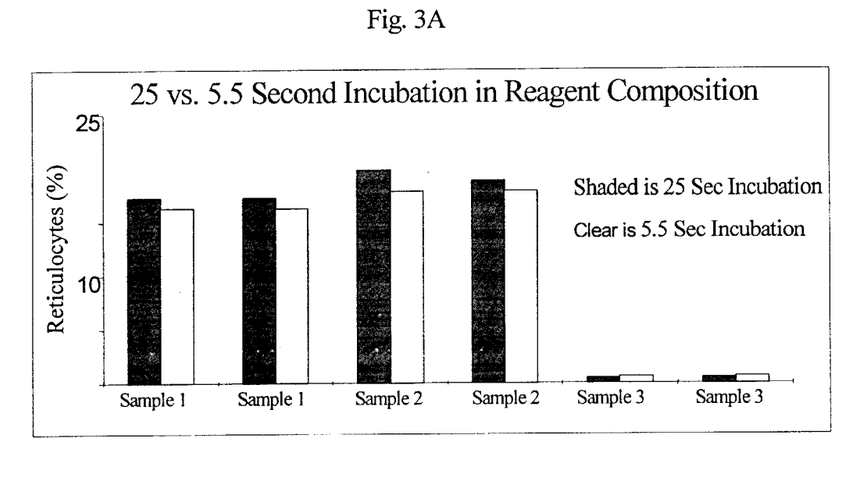
FIGS. 3A–3B are a histogram and graph for the identification of reticulated platelets according to Example III.

Forward light scatter (FS), side scatter (SS) and red fluorescence (FL) parameters were measured to analyze reticulated cells. FIG. 3A shows that the time of incubation can be reduced to approximately 5.5 seconds from 25 seconds and obtain comparable reticulocyte enumeration. Results are reported from duplicate analysis. Samples 1 and 2 represent abnormal high reticulocyte counts in blood cell samples 1 and 2, respectively, and sample 3 represents a normal reticulocyte count in a blood cell sample from a screened normal donor.

Figure 3B:
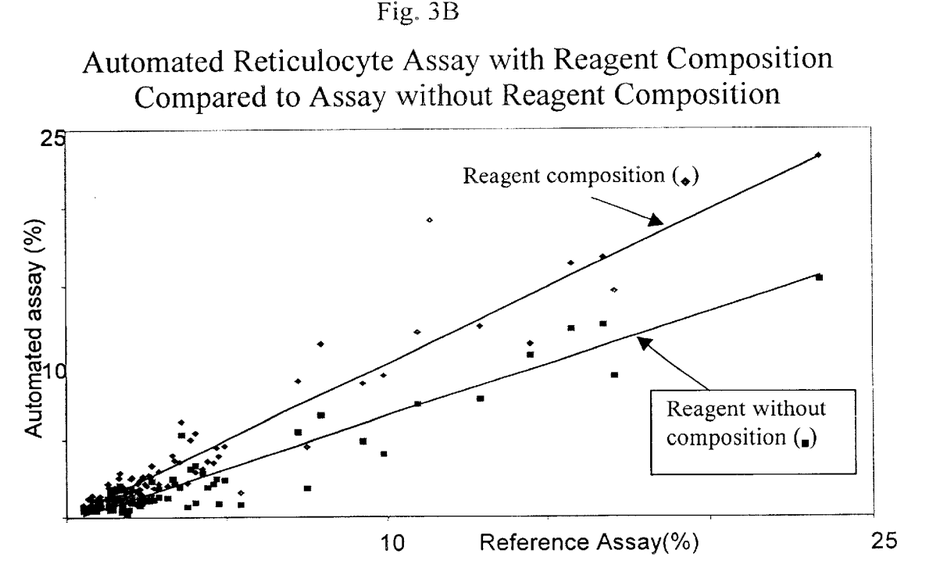

FIG. 3B shows a comparison of a reticulated cell assay of the reagent composition of this invention compared to a reticulated cell assay of a reagent without a sphering agent. The resulting data demonstrates a linearity to a referenced reticulocyte assay using thiazole orange. It is shown that the slope of the reagent composition is essentially a value of 1, indicating a correlation with the referenced method.

Accordingly, the figures demonstrate that the method of this invention can be performed within 25 seconds with accuracy to the referenced method.

EXAMPLE IV METHOD OF ANALYSIS OF RETICULATED PLATELETS AND MATURE PLATELETS

Figure 5:
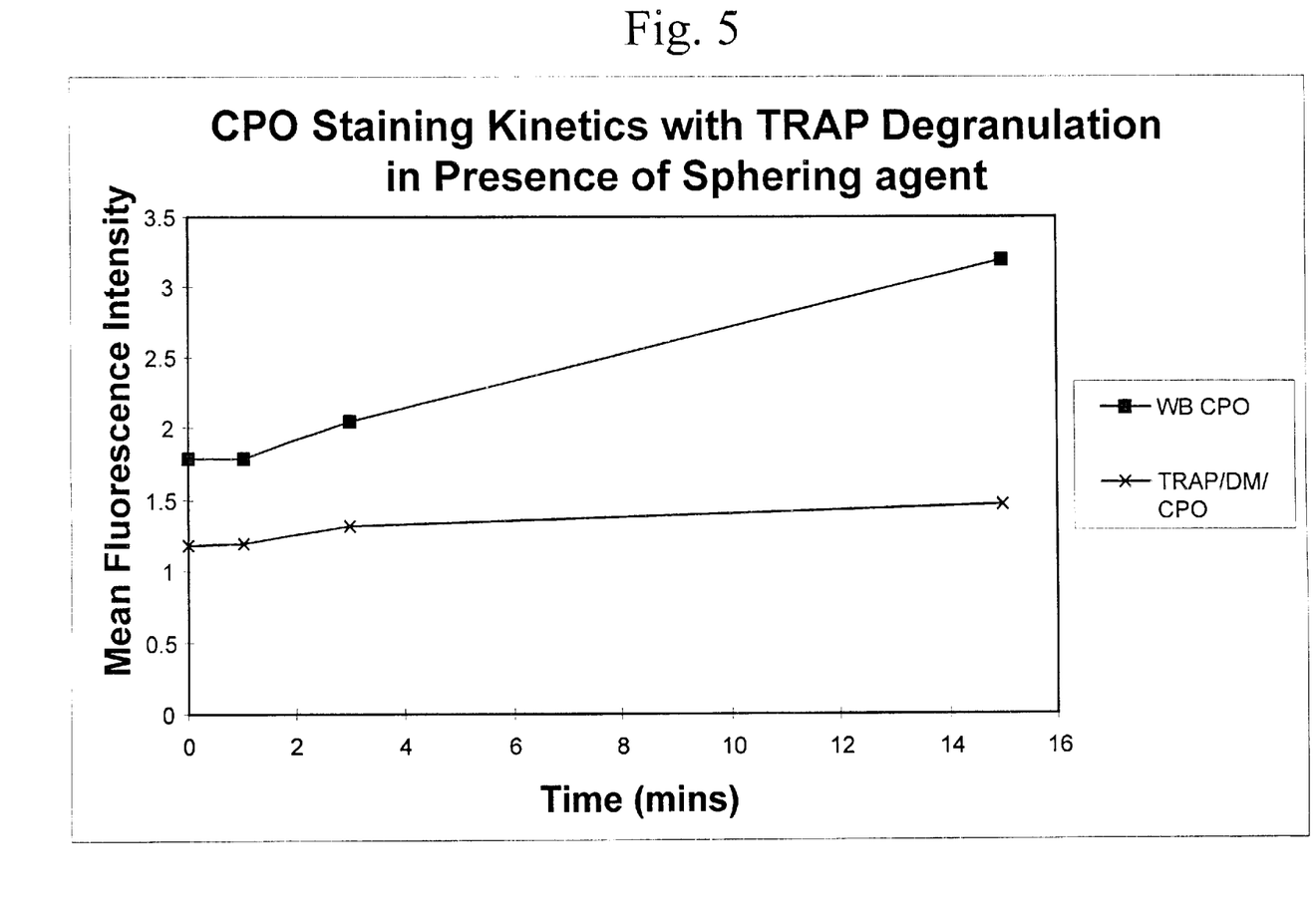
FIG. 5 is a graph of the mean fluorescence intensity of the platelet population against time of incubation according to Example IV.

FIG. 5 is a determination of staining kinetics using coriphosphine-O. In one analysis, a degranulating agent is added to a whole blood sample to degranulate the ADP found in the dense granules contained in the reticulated platelets and mature platelets, and in the second analysis the degranulating agent is not used. In this example, the degranulating agent is thrombin receptor activating protein (TRAP).

It is known that the reticulated platelets contain RNA, but the mature platelets do not contain RNA. Consequently, by graphing the mean fluorescence intensity of the platelet population against the time of incubation, a determination of the contribution of the ADP staining to total staining can be made. This enables the differentiation between the reticulated platelets and mature platelets to be obtained.

The invention has been described with reference to particularly preferred embodiments. It will be appreciated, however, that various changes can be made without departing from the spirit of the invention, and such changes are intended to fall within the scope of the claims.

What is claimed is:

1. A method for identifying reticulated cells in a blood cell sample containing reticulated cells and non reticulated blood cells on an automated hematology analyzer comprising:
   a. mixing a blood cell sample containing reticulated cells with a reagent composition comprising a metachromatic dye and a sphering agent to form a suspension of cells;
   b. incubating the suspension of cells for less than thirty (30) seconds to allow the reagent composition to stain single stranded and double stranded nucleic acid contained in the blood cells;
   c. exciting said suspension of cells with light excitation wavelength;
   d. measuring the presence of a first fluorescence signal in the suspension of cells, against the presence of a second fluorescence signal gated on at least one parameter selected from the group consisting of light scatter, direct current, radio frequency and fluorescence, said at least one parameter being used to identify leukocytes, erythrocytes, and thrombocytes; and
   e. identifying the number of reticulated cells in the sample from said measurement.

2. The method of claim 1, wherein the reticulated cells comprises reticulated platelets.

3. The method of claim 1, wherein the reticulated cells comprises reticulocytes.

4. The method of claim 1, wherein said at least one parameter being used to identify leukocytes, erythrocytes, and thrombocytes comprises light scatter.

5. The method of claim 1, wherein the dye comprises coriphosphine-O.

6. The method of claim 1, wherein the sphering agent comprises an alkyl amido betaine, an alkyl betaine, N-tetradecyl-N-, N-dimethyl-3-ammonio-1-propanesulfonate, N-dodecyl-N,N-dimethyl-3-ammonio-1-propanesulfonate, n-dodceyl-D-maltoside, n-tetradecyl-D-maltoside, decanoyl-N-methyl-glucamide, n-dodecyl-D-glucopyranoside or n-decyl-D-glucopyranoside.

7. The method of claim 6 wherein the sphering agent comprises dodecyl-$\beta$-D-maltoside.

8. The method according to claim 6, wherein the sample is excited and fluorescence is measured by means of a flow cytometer, wherein said incubated blood sample is caused to pass through a sensing zone of an automated analyzer.

9. The method of claim 1 wherein the blood sample is whole blood.

10. The method of claim 1 which further comprises determining cell by cell hemoglobin concentration of blood cells contained in the sample.

* * * * *